(12) United States Patent
Choudhury et al.

(10) Patent No.: US 8,480,645 B1
(45) Date of Patent: Jul. 9, 2013

(54) MULTI-DOSE DEVICE FOR INSERTION INTO A VIAL AND METHOD OF USING THE SAME

(76) Inventors: Sambhu N. Choudhury, Cincinnati, OH (US); Sean M. Lynch, Cincinnati, OH (US); Arturo David Sanchez, Lebanon, OH (US); Gordon Edgar Atkinson, Hickory, NC (US)

( * ) Notice: Subject to any disclaimer, the term of this patent is extended or adjusted under 35 U.S.C. 154(b) by 486 days.

(21) Appl. No.: 12/546,411

(22) Filed: Aug. 24, 2009

Related U.S. Application Data

(60) Provisional application No. 61/091,073, filed on Aug. 22, 2008.

(51) Int. Cl.
*A61M 5/32* (2006.01)

(52) U.S. Cl.
CPC .................................. *A61M 5/3297* (2013.01)
USPC .......................................... 604/411; 604/405

(58) Field of Classification Search
USPC .......................................... 604/405, 411, 414
See application file for complete search history.

(56) References Cited

U.S. PATENT DOCUMENTS

| | | | | |
|---|---|---|---|---|
| 2,342,215 A | | 2/1944 | Perelson | |
| 2,541,272 A | * | 2/1951 | Murphy | 141/285 |
| 3,063,451 A | * | 11/1962 | Kowalk | 600/576 |
| 3,608,550 A | * | 9/1971 | Stawski | 604/414 |
| 3,662,752 A | * | 5/1972 | Yokoyama | 604/411 |
| 3,938,520 A | * | 2/1976 | Scislowicz et al. | 604/405 |
| 4,058,121 A | * | 11/1977 | Choksi et al. | 604/411 |
| 4,066,079 A | * | 1/1978 | Chiarolla | 604/190 |
| 4,128,098 A | * | 12/1978 | Bloom et al. | 604/406 |
| 4,393,864 A | | 7/1983 | Galkin et al. | |
| 4,511,359 A | * | 4/1985 | Vaillancourt | 604/411 |
| 4,543,101 A | * | 9/1985 | Crouch | 604/411 |
| 4,610,683 A | * | 9/1986 | Vaillancourt | 604/405 |
| 4,723,955 A | * | 2/1988 | Vaillancourt | 604/405 |
| 4,765,588 A | * | 8/1988 | Atkinson | 251/149.1 |
| 4,787,898 A | * | 11/1988 | Raines | 604/411 |
| 5,041,106 A | * | 8/1991 | Noji et al. | 604/411 |
| 5,224,937 A | * | 7/1993 | van der Heiden et al. | 604/200 |
| 5,423,791 A | | 6/1995 | Bartlett | |
| 5,676,346 A | * | 10/1997 | Leinsing | 251/149.1 |
| 5,839,715 A | * | 11/1998 | Leinsing | 251/149.1 |
| 5,874,048 A | * | 2/1999 | Seto et al. | 422/519 |
| 5,924,584 A | | 7/1999 | Hellstrom et al. | |
| 7,077,176 B2 | | 7/2006 | Py | |
| 7,306,129 B2 | | 12/2007 | Swiss et al. | |
| 2004/0124388 A1 | * | 7/2004 | Kiehne | 251/149.1 |
| 2005/0131357 A1 | * | 6/2005 | Denton et al. | 604/275 |
| 2006/0106360 A1 | * | 5/2006 | Wong | 604/411 |
| 2008/0172024 A1 | * | 7/2008 | Yow | 604/411 |

\* cited by examiner

*Primary Examiner* — Melanie Hand
*Assistant Examiner* — Paula Craig
(74) *Attorney, Agent, or Firm* — Jenei LLC

(57) ABSTRACT

The present invention is a multi-dose device for insertion into a vial containing a fluid. The device has a double-nested needle inserter for insertion into the vial. Opposite the double-nested needle inserter is an air opening stack and a Luer lock port.

4 Claims, 3 Drawing Sheets

MULTI-DOSE DEVICE FOR INSERTION INTO A VIAL AND METHOD OF USING THE SAME

CROSS-REFERENCE TO RELATED APPLICATION

The present application claims priority to U.S. Patent Application No. 61/091,073 as filed Aug. 22, 2008.

STATEMENT REGARDING FEDERALLY SPONSORED RESEARCH

Not applicable.

NAMES OF THE PARTIES TO A JOINT RESEARCH AGREEMENT

Not applicable.

INCORPORATION-BY-REFERENCE OF MATERIAL SUBMITTED ON A COMPACT DISC

Not applicable.

BACKGROUND ON THE INVENTION

1. Field of the Invention

The present invention relates generally to containers for storing and dispensing medicines, and more particularly to devices allowing the substances to be dispensed there from with substantially little to no contamination of the substances within the containers.

2. Description of the Related Art

Vials with medicine are provided for use for home, doctor's offices, emergency rooms, operating rooms, community clinics, and local hospitals. These vials are sometimes for single usage. Often, however, the contents of the vials may be used for multiple uses in one or more patients.

The usual method for removing fluid from such vials is to inject air into the vial and remove a commensurate amount of fluid. The vial often has a rubber top that allows insertion of a needle or syringe into the interior of the vial and subsequent removal of a portion or more the fluid contents.

An inherent problem with multiple uses of such vials is possible contamination of the fluid contents of the vial with a contaminated syringe. The syringe may be contaminated with benign elements including, for example, saline or additional medications. Unfortunately, the syringe may be also contaminated with, for example, blood and/or other body fluids from the same or other individual. Such contamination of the fluid contents can then potentially spread disease and infection to one or more individuals.

The most basic solution to the aforementioned possible contamination problem would be to never have multiple use vials. This is inherently a way to prevent the problem altogether; however, would result in wasted processing of additional medications and additional garbage that would further clutter the environment.

Multi-dose vial caps are present currently in a form that does not use needles. Such caps usually allow attachment of a syringe to a Luer lock adaptor to the cap on the vial so that additional needles are not wasted.

A Luer lock connection generally includes a male Luer connector with a tapered conical portion that is adapted to fit into a correspondingly shaped receptacle of a female Luer connector (i.e., a hub). A spin nut is commonly disposed on the male Luer connector and is rotatable relative to the tapered conical portion. The spin nut includes internal threads that are adapted to engage external threads on the female Luer connector to lock together the Luer connectors. When properly engaged, the conical portion fits tightly within the receptacle to produce a sealed interconnection.

However, use of a Luer lock connection in and of itself does not prevent contamination.

SUMMARY

Various exemplary embodiments of the present invention include a multi-dose device for insertion into a vial. The device is comprised of an air opening stack, a Luer lock port, and a double-nested needle inserter on a side of the device opposite the air opening stack and the Luer lock port. The double-nested needle inserter is comprised of an inner needle inserter substantially surrounded by an outer needle inserter.

The exemplary embodiments of the present invention further include a method of removing fluid contents from a vial. The method is comprised of inserting a multi-dose device into a vial via a double-nested needle inserter of the device. The device is comprised of an air opening stack, a Luer lock port, and a double-nested needle inserter on a side of the device opposite the air opening stack and the Luer lock port. The double-nested needle inserter is comprised of an inner needle inserter substantially surrounded by an outer needle inserter. Then a Luer lock syringe is connected to the Luer lock port, and the syringe is filled with a desired amount of fluid from the vial by pulling air through the inner needle inserter and into the vial as the syringe aspirates the fluid from the vial through the outer needle through the Luer lock port and into the syringe.

BRIEF DESCRIPTION OF THE DRAWINGS

The various exemplary embodiments of the present invention, which will become more apparent as the description proceeds, are described in the following detailed description in conjunction with the accompanying drawings, in which.

DESCRIPTION OF THE REFERENCED NUMERALS

Figure 1:
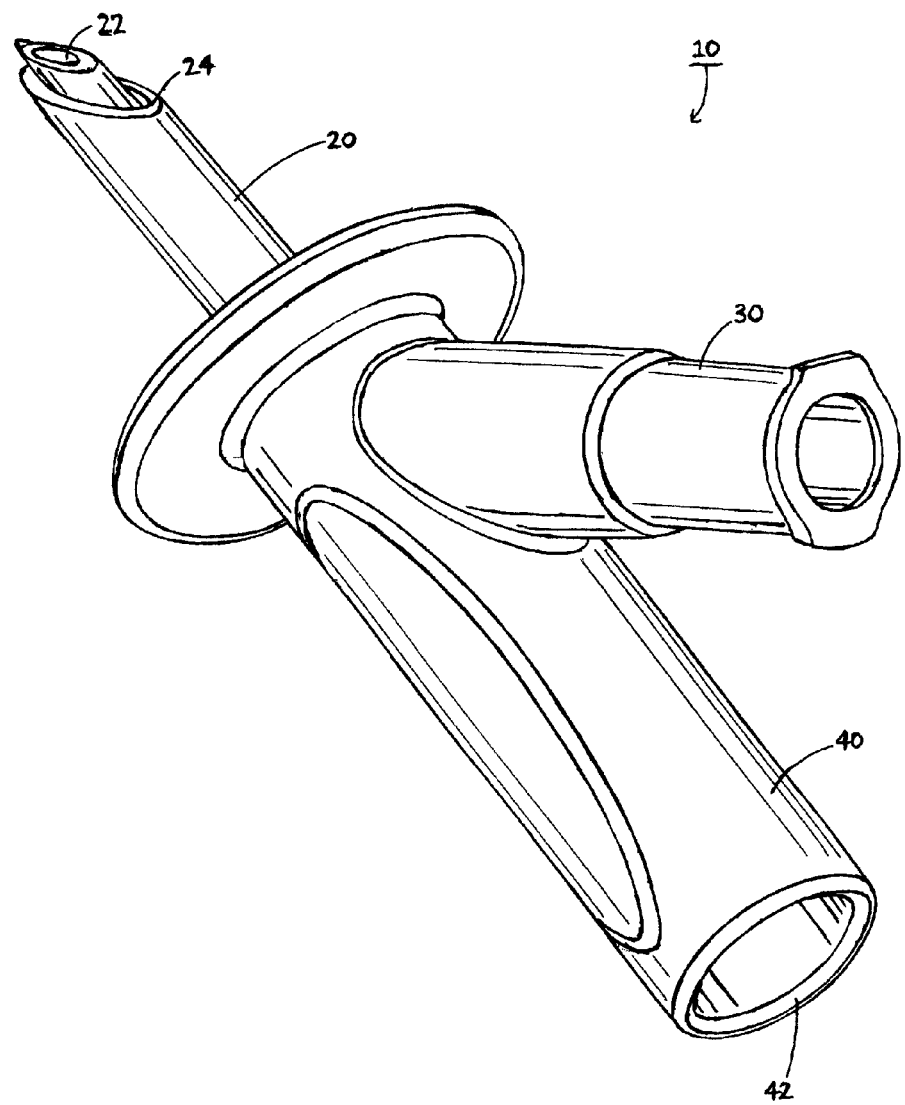
FIG. 1 is a perspective view illustration of an exemplary embodiment of a multi-dose device according to the present invention.

In reference to the drawings, similar reference characters denote similar elements throughout all the drawings. The following is a list of the reference characters and associated element:

10 Multi-dose device
20 Double-nested needle inserter
22 Inner needle inserter
24 Outer needle inserter
30 Luer lock port
32 One-way valve
40 Air stack opening
42 Filter

DETAILED DESCRIPTION

Exemplary embodiments of the present invention are directed to a device and method of using the same device to substantially limit and avoid contamination of a multi-use vial.

Figure 2:
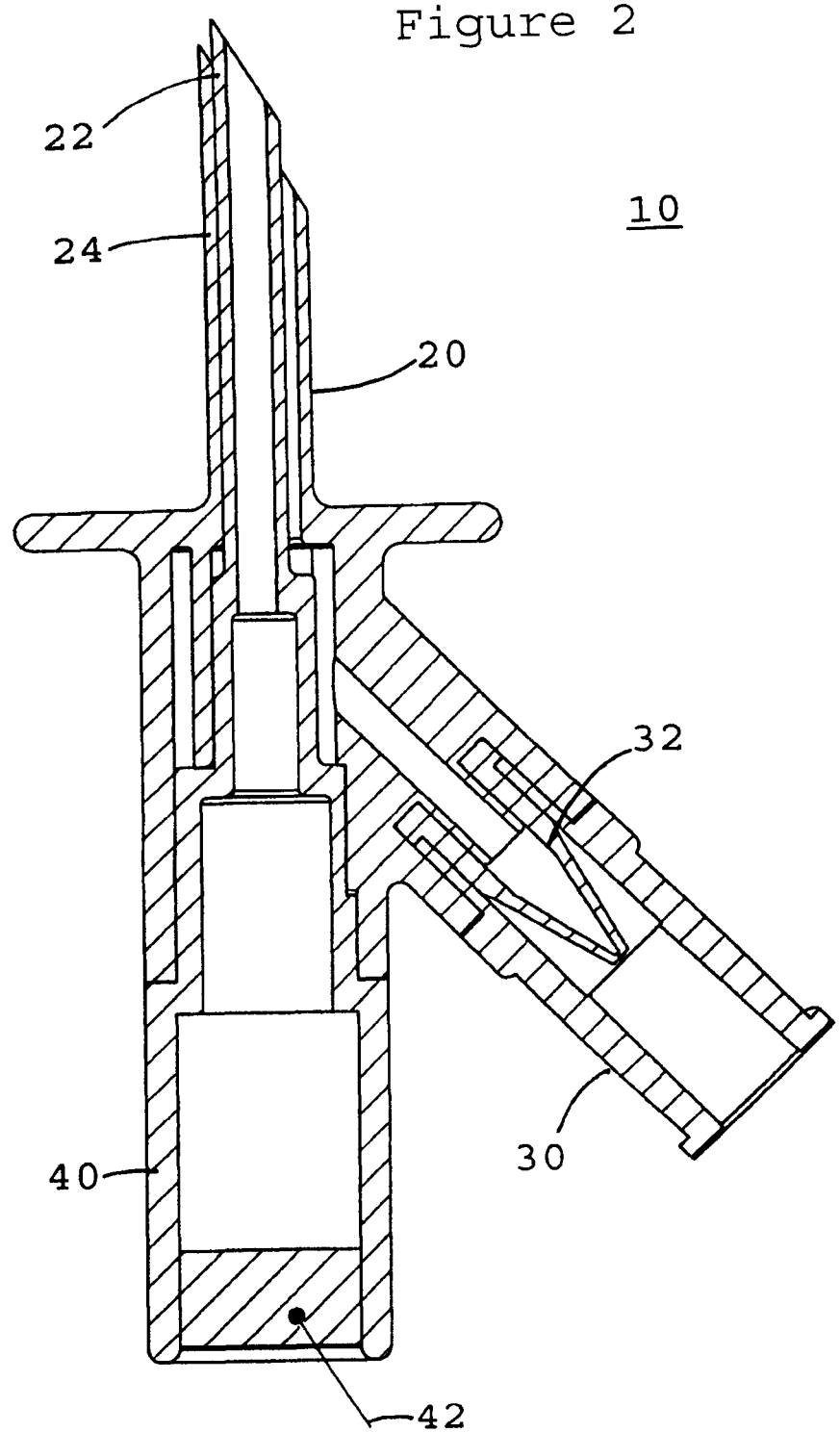
FIG. 2 is a side view cut-away illustration of an exemplary embodiment of a multi-dose device according to the present invention.
Figure 3:
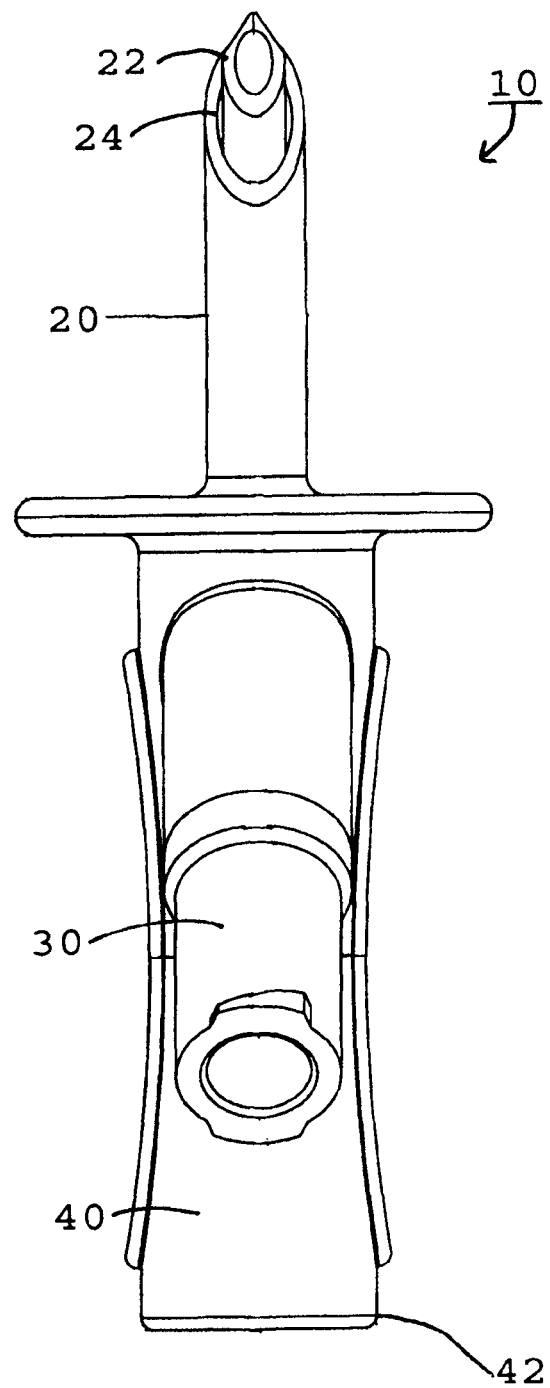
FIG. 3 is a front view cut-away illustration of an exemplary embodiment of a multi-dose device according to the present invention.

As illustrated in FIGS. 1-3, the various exemplary embodiments of the present multi-dose device 10 include a double-nested needle inserter 20 comprised of an inner needle inserter 22 and an outer needle inserter 24. Such arrangement of an inner needle inserter and an outer needle inserter allows one to aspirate from a vial (not shown) and allows air to be aspirated into the vial through separate access points for each needle inserter.

The inner needle inserter is substantially surrounded by the outer needle inserter. A base of the double-nested needle inserter is preferably pointed so as to pierce a top of a vial.

The exemplary embodiments of the present device further include a Luer lock port 30 and an air opening stack 40. The Luer lock port and the air opening stack are on a side of the device opposite of the double-nested needle inserter.

The air stack opening connects to the inner needle inserter.

One or more filters 42 may be positioned in, over, or a combination there of, the air stack opening.

The Luer lock port connects to the outer needle inserter.

The Luer lock port preferably includes a one-way valve 32 that does not allow injection of air or fluid into the vial via the Luer lock port. Thus, contaminants from a syringe (not shown) attached at the Luer lock port are prevented from entering the vial when drawing fluid therefrom.

In exemplary embodiments of the present invention, the double-nested needle inserter is injected into a vial. A Luer lock syringe (not shown) is connected to the Luer lock port. A plunger (not shown) on the Luer lock syringe is moved to fill the syringe with the desired amount of fluid from the vial. In filling the syringe, air is pulled through the inner needle inserter and into the vial as the syringe aspirates through the outer needle. The air entering the air stack opening and into the inner needle inserter is preferably pulled through one or more filters to prevent contamination from the air.

The multi-dose device can be kept on a vial presumably for an indefinite period of time as the Luer lock port can be capped and stored. The air stack opening may also be capped and stored.

While this invention has been described in conjunction with the specific embodiments outlined above, it is evident that many alternatives, modifications and variations will be apparent to those skilled in the art. Accordingly, the preferred embodiments of the invention as set forth above are intended to be illustrative, not limiting. Various changes may be made without departing from the spirit and scope of the invention.

What is claimed is:

1. An multi-dose device for insertion into a vial, the device being comprised of:
   an air opening stack;
   a Luer lock port comprising a one-way valve configured such that the valve does not allow injection of air or fluid into the vial via the Luer lock port; and
   a double-nested needle inserter on a side of the device opposite the air opening stack and the Luer lock port,
   wherein the double-nested needle inserter is comprised of an inner needle inserter substantially surrounded by an outer needle inserter and wherein a base of the double-nested needle inserter is shaped to allow piercing a vial;
   wherein the inner needle inserter and outer needle inserter are configured to allow aspiration from a vial and simultaneously allow air to be aspirated into the vial through separate access points for each needle inserter; and
   wherein the air opening stack connects to one needle inserter and the Luer lock port connects to the other needle inserter.

2. The multi-dose device according to claim 1, wherein the air opening stack includes one or more filters.

3. The multi-dose device according to claim 2, wherein the Luer lock port is in fluid connection with the outer needle inserter and wherein the air stack opening is in fluid connection with the inner needle inserter.

4. The multi-dose device according to claim 2, wherein the air opening stack includes one or more filters configured such that contaminants from the inflow of air upon aspiration are prevented from entering the vial when drawing fluid.

\* \* \* \* \*